(12) United States Patent
Horvath

(10) Patent No.: US 7,040,894 B2
(45) Date of Patent: May 9, 2006

(54) RUBBER DAM

(75) Inventor: Domonkos Horvath, Jestetten (DE)

(73) Assignee: Ivoclar Vivadent AG, Schaan (LI)

( * ) Notice: Subject to any disclaimer, the term of this patent is extended or adjusted under 35 U.S.C. 154(b) by 107 days.

(21) Appl. No.: 10/468,957

(22) PCT Filed: May 27, 2002

(86) PCT No.: PCT/EP02/05793

§ 371 (c)(1),
(2), (4) Date: Aug. 22, 2003

(87) PCT Pub. No.: WO02/096313

PCT Pub. Date: Dec. 5, 2002

(65) Prior Publication Data

US 2004/0072126 A1    Apr. 15, 2004

(30) Foreign Application Priority Data

May 30, 2001 (DE) .................................. 101 26 179

(51) Int. Cl.
*A61C 5/12* (2006.01)
(52) U.S. Cl. ..................................................... 433/136
(58) Field of Classification Search ................ 433/136, 433/137, 138, 139
See application file for complete search history.

(56) References Cited

U.S. PATENT DOCUMENTS

| | | | | |
|---|---|---|---|---|
| 4,544,357 A | * | 10/1985 | Williams | 433/136 |
| 4,695,253 A | * | 9/1987 | Tysse | 433/136 |
| 5,931,673 A | * | 8/1999 | Bolbolan | 433/136 |
| 6,648,642 B1 | * | 11/2003 | Horvath et al. | 433/136 |
| 2003/0087216 A1 | | 5/2003 | Heasley | |
| 2003/0190584 A1 | | 10/2003 | Heasley | |
| 2004/0126739 A1 | | 7/2004 | Heasley | |
| 2004/0170945 A1 | | 9/2004 | Heasley | |
| 2004/0209224 A1 | | 10/2004 | Heasley | |
| 2004/0219486 A1 | | 11/2004 | Heasley | |

OTHER PUBLICATIONS

U.S. Patent Appl. 11/194,639.
U.S. Provisional Patent Appl. 60/281,862.

* cited by examiner

*Primary Examiner*—Cary E. O'Connor
(74) *Attorney, Agent, or Firm*—Nixon Peabody LLP

(57) ABSTRACT

A rubber dam for isolating one or more teeth in a patient's mouth includes an annular perioral frame (2) to be arranged extraorally, an elastic and film-like cover (1) connected to the frame (2) and which in the untensioned state has a bag-shaped section (3) for insertion into the oral cavity, and a fastener (6) for the intraoral fastening of the cover (1). The fastener (6) is formed by an elastic annular element (6) insertable into the vestibule (8) in an elastically deformed state and then exerts a force on the cover (1) pushing and firmly retaining it in the vestibule (8). When the rubber dam is inserted, the cover (1) extends in a slightly tensioned state between the frame (2) and the fastener (6) located in the vestibule (8) around the corners of the mouth and the lips (7) and intraorally in the upper and lower jaw in a slightly tensioned state out of the vestibule (8), over the front sides of the teeth and in the palate and tongue area in the plane of the chewing surfaces, and pushes the lips, the corners of the mouth and the cheeks away from the teeth as well as the jaws apart, assisting the opening of the mouth.

36 Claims, 8 Drawing Sheets

RUBBER DAM

This application is a national stage application under 35 U.S.C. § 371 from PCT Application No. PCT/EP02/05793 filed May 27, 2002, which claims the priority benefit of German application 101 26 179.9 filed May 30, 2001.

The present invention relates to a rubber dam for the isolation of a tooth or several teeth in a patient's mouth according to the preamble of claim 1.

In dental practice it is necessary to carry out clean and dry treatments of teeth, as well as to isolate the teeth concerned. For this purpose, the so-called rubber dam has been known for approximately 150 years. In its original and simplest form, it consists of an elastic, flat covering means, mostly in the form of a rubber cloth, which is fastened in a frame outside the mouth. In order to isolate one or more teeth, the covering means is pushed elastically into the oral cavity and towards the teeth concerned. By means of a selective perforation, the covering means can then be pulled over a tooth, wherein the edge of the hole formed in the elastic covering means rests against the tooth and in this way ensures a circular seal around the tooth against fluids, such as for example saliva or blood. By fastening the covering means to the tooth, it is reciprocally anchored against the frame which is arranged outside the mouth and into which the covering means is clamped. The elasticity of the covering means causes the frame to be pushed firmly against the face and the covering means to be fixed extraorally in a stable manner. The high wall tensions which occur prevent the covering means from being unintentionally sucked in by a dental suction device during sucking off.

In addition to the named tasks, this known rubber dam also represents a hygienic barrier and thus a protection against infectious diseases both for the patient and for the dentist and his assistants. Furthermore, it offers toxic protection against drilled-out amalgam or chemicals used by the dentist, such as disinfectants, and prevents the swallowing or aspirating of items, such as for example broken-off drill bits or tips of dangerous small instruments. As a result of the isolation of the operation field known from surgery, the rubber dam makes it easier for the dentist to concentrate. Further important advantages are a reduced treatment time, the elimination of frequent rinsing of the patient, the exclusion of moist breath with the result that the reconstructive materials used can be processed in a physically optimum manner, and the prevention of bad breath which irritates the person performing the treatment.

When the described rubber dam is used, the covering means takes the shape of a funnel and is strongly stretched, in particular when the lateral teeth and above all the rear molars are treated. Due to the high tension, the covering means must be fastened in the mouth to one or more teeth with the help of a strong clamp, with the risk that the teeth concerned are irreversibly damaged by the clamps. Even with the most varied methods of anchoring to the frame, the wall tension of the covering means can be only poorly controlled. If the covering means is anchored only loosely to the frame, troublesome heavy creases occur, the covering means is easily drawn into a suction device and the whole fit becomes unstable a s a result of the low tension. If it is thus desired for example to avoid a troublesome creasing, the two-dimensional covering means must be substantially stretched with the named results. The dentist who—due to the size of the oral cavity—must carry out complicated treatments in any case in narrow spatial conditions, needs the largest space that is anatomically possible without limitations. As a result of the funnel shape of the covering means, the available space is so drastically reduced that treatment with dental instruments, such as for example turbines, mirrors or suction devices, is possible only to a limited extent or often even impossible when using a rubber dam. These limitations are for example illustrated in an immediately apparent manner in the book "Kofferdam in Theorie und Praxis" [Rubber dam in theory and practice], Reinhard Winkler, Quintessenz-Verlags GmbH, 1991, pages 47 and 56 ("angelegter Kofferdam" [fitted rubber dam]). In addition, with this isolation technique the whole oral vestibule is obstructed, covered and sealed. Furthermore, the covering means leading out of the oral cavity in a straight line offers no means of retaining accumulations of fluid, so that fluid, if it is not immediately sucked off, runs out of the rubber dam and the mouth in an uncontrolled manner. Moreover, the fitted rubber dam causes the lips to be heavily pressed down or pressed flat and not a selective vertical upward pressing which ensures that the upper or lower lip is kept away or retracted, which is important for the dentist, and clears the way for the treatment of the teeth lying behind. Finally, patient acceptance is also not very high because of the external appearance of the fitted rubber dam (cf. also "Kofferdam in Theorie und Praxis", see above, Figure 477: "Fertige Isolation" [Completed isolation]).

The named problems of rubber dam systems, which are based on the described method of operation of a funnel-shaped, reciprocally stressed covering means between the clamped tooth and the extraoral frame, have not been solved despite a variety of different and numerous modifications to the frame, such as for example the choice of a round or square shape, to the covering means, such as for example the choice of different materials and strengths, and to the clamps. For these reasons, the rubber dam has not gained acceptance to date in dental treatment practice despite the above-mentioned and many other advantages. World-wide it is not used by most dentists or only used in certain treatments, such as for example in endodontology for forensic reasons or in restorative treatments on the easily accessible front teeth. Even in industrialized countries the rate of use is under 10%.

Another rubber dam is known from U.S. Pat. No. 5,340,313. This rubber dam has a bulge in the oral cavity, which renders the high tension of the covering means superfluous. A dimensionally stable housing is used in order to keep the treatment space clear. Precisely these are very restricting and are not at all suitable for the wide variety of treatments with dental instruments. In addition, a wide variety of shapes and sizes is required in order to treat all patients. As soon as dimensionally stable items are inserted into the oral cavity, disadvantages prevail, such as for example the restriction of freedom of movement and of the treatment space combined with the lack of a clear view, an expensive production or a failure to take into account the individual anatomy. The above-described problems are solved only insufficiently by this rubber dam.

In U.S. Pat. No. 4,889,490 a face mask for dental treatment is disclosed which has a customary mask frame around which supports are arranged which are fastened to same, on which supports is fixed a film with an opening for the mouth. The mask frame can be pressed together and inserted between the lips, so that after being released it pushes the lips apart laterally. The film serves to protect the patient's face from particles or fluids flying around. This device does not serve to isolate and dry out one or more teeth and pushes the lips apart merely laterally, the hard profile also interfering with the treatment, as the tissue dynamic which is important in this area is lost.

U.S. Pat. No. 2,680,908 describes a rubber dam which comprises complicated shaping retaining elements. These are expensive to produce and, as dimensionally stable elements, have the above-named disadvantages.

DE 299 06 369 U1 describes a dental shielding device with a shielding film which has an oral-cavity eversion that is adapted to the shape of the oral cavity. The film is designed such that it can be inserted unstretched into the oral cavity and remains essentially unstretched—apart from the expansion in the area of the tooth to be treated—even after the perforated film is pulled over a tooth. Therefore the film does not withstand a sucking off, but collapses and is sucked in as soon as a suction device comes near the wall. In order to prevent this, a strengthening of the eversion by material reinforcements or ribs is proposed, which however is associated with a complicated and expensive production and the above-described disadvantages of dimensionally stable parts. Attachment to the face is carried out for example with the help of elastic bands which are placed around the ears, or a retaining device passing around the head. In addition to the complicated design, the awkward handling and discomfort for the patient, the lips are only pressed down, but not kept away or retracted in a targeted manner. Furthermore, the film lying untensioned in the oral cavity is resting against the palate and the tongue. This not only has the disadvantage that patients find this wallpaper-like lining of the palate and the limited mobility of the tongue unpleasant (claustrophobia), but also that a gag reflex is triggered in patients who react extremely sensitively.

Further rubber dam designs, each being fixed to the teeth in the oral cavity essentially in the shape of an untensioned bag, also have the same disadvantages and are disclosed in DE 197 04 904 and WO 98/34559.

The object of the present invention is to design a rubber dam for the isolation of a tooth in a patient's mouth such that it can have unlimited use in dental practice and the named disadvantages are eliminated.

The features of claim 1 serve to achieve this object. Advantageous embodiments of the rubber dam are the subject of the respective dependent claims.

The basic idea of the present invention is that the rubber dam comprises an annular frame for resting against the perioral facial area, an elastic film-like covering means which can be connected to the frame and in an untensioned state has a bag-shaped section for insertion into the oral cavity, and a fastening means for the intraoral fastening of the covering means, the fastening means being formed by an elastic and annular element which is adapted in order to be inserted in an elastically deformed state into the vestibule and to exert a force on the covering means which pushes the covering means into the vestibule and retains it therein, so that, when the rubber dam is inserted, the covering means extends in a slightly tensioned state between the extraoral frame and the fastening means located in the vestibule around the lips and the corners of the mouth and intraorally, in the upper jaw and in the lower jaw, in a slightly tensioned state out of the vestibule, over the external surfaces and the chewing surfaces of the teeth and in the palate and tongue area in the plane of the chewing surfaces, and the lips, cheeks and corners of the mouth are pushed away from the teeth and a force directed upward is exerted on the upper jaw and a force directed downward is exerted on the lower jaw. The shape of the bag-shaped section can vary to a large extent and have any desired three-dimensional shape with an opening. The only deviation from the described course of the covering means is in the area of the teeth to be treated, in which the covering means is perforated and pulled over one or more teeth.

The rubber dam according to the invention therefore consists of a passive, simple shape comprising an elastic covering means and a perioral frame which are brought into a dynamic shape with the help of an elastic and annular fastening means to be clamped into the vestibule, wherein the three-dimensional shape of the oral cavity is accommodated by a slight stretching of the covering means and thus size differences and an individual anatomy are taken into account.

The annular fastening means inserted into the vestibule, together with the covering means, advantageously causes the cheeks and the corners of the mouth to be pushed apart transversally and the upper and lower jaw as well as the lips to be pushed apart vertically. To this end, the covering means is fixed extraorally by the perioral frame, while intraorally the annular fastening means in the vestibule effects a further fixing of the covering means, so that the slightly tensioned covering means lying in between extends around the lips and the corners of the mouth and in abutment to these, as a result of which forces are exerted by the slightly stretched covering means on all the perioral structures that push these radially apart. The annular fastening means follows the course of the vestibule preferably up to the rearmost molars. In the lower jaw and the upper jaw, the covering means extends in a slightly tensioned state between the fixing in the vestibule over the front sides of the teeth and the chewing surfaces of the teeth in the plane of the chewing surfaces. The only deviation from this course is in the area of the teeth to be treated, in which area the covering means is perforated and pulled over the teeth. In this way, the fastening means, pushing itself into the vestibule due to its elasticity, effects that it pushes the jaws apart either itself by pressing directly onto the oral mucous membrane or via the slightly stretched covering means, which exerts corresponding forces on: the chewing surfaces of the teeth and on the lips, or by a co-operation of these forces. As a result of the described arrangement, for one thing a force directed spherically outwards is therefore transferred to the lips and the corners of the mouth by the covering means, the force vectors being ideally arranged to effect a circular retraction of the lips and the corners of the mouth. This is advantageous both for the dentist and for the patient. Thus it offers the dentist optimum conditions for all types of dental treatment. Due to the lips and the corners of the mouth being gently pushed apart or retracted, the teeth to be treated become visible. Nevertheless, the mobility of the perioral tissue is maintained and the lips and the corners of the mouth remain deformable according to the treatment requirement. Dimensionally stable shields and retracting elements are thus not necessary for this task. As the covering means is thin and elastic, a lip or a corner of the mouth can—if necessary—be retracted or kept away even further with instruments. Furthermore, the described forces pushing the jaws apart give the patient a pleasant feeling because they help him to open his mouth and also to keep it open over a long period without difficulty.

When the rubber dam is inserted, the forces exerted by the annular fastening means through its spring effect are therefore transferred vertically, transversally and sagitally indirectly or essentially indirectly to the oral cavity, in that after insertion into the vestibule the rubber dam produces a tension in the whole covering means, i.e. the wall of the rubber dam. In this tensioned state, the covering means, which is open at the front and closed towards the throat, surrounds the lips and the corners of the mouth in a circular manner starting from the extraoral frame, and extends into the vestibule, out of this again and—with the exception of the areas in which the covering means is perforated and pulled over the teeth—over the external and chewing surfaces of the teeth, and covers the tongue and the palate in the chewing plane. As a result of this course taken by the covering means, the lips, the corners of the mouth, the cheeks and the mouth are kept apart and sagital forces stabilize the rubber dam due to the reciprocal tensioning between the extraoral fixing provided by the periorial frame and the intraoral fixing provided by the fastening means.

When using the rubber dam according to the invention, the maximum size of the oral cavity is isolated so that the largest possible isolation area is formed without interfering elements. The retracted cheeks, lips and corners of the mouth substantially enlarge the vestibule which is covered in a circular manner by the elastic covering means up to deep into the vestibule and offers direct access to the teeth.

As the covering means in the lower jaw covers the floor of the mouth and the tongue in the plane of the chewing surfaces of the teeth, a free space remains for the tongue, which is very important for patients as the swallowing process can be carried out unhindered and the tongue is gently kept away by the covering. In the upper jaw, the covering of the hard and soft palate in the plane of the chewing surfaces brings about that unpleasant sensations caused by a contact between the palate and the covering means are avoided and patients with a gag reflex are given particular consideration by ensuring a gentle treatment.

As a result of the only low tension of the covering means, it can be impressed if necessary both in the upper and lower jaw, for example in order to create space for suction devices or other instruments. Through the elastic tensioning force of the annular fastening means which pushes the stretchable covering means into the vestibule in a uniform and circular manner, creasing is largely avoided.

The covering means is also held such that after perforation it naturally slips around the tooth and is pulled downward by the elastic annular fastening means. In contrast to this, with the previously known rubber dam, in which a flat covering means in the form of a rubber cloth is pulled up to the lateral molars, pull forces occur which attempt to pull the covering means off the tooth, so that broad and strong retaining clamps are necessary. It is clear that an elastic, spatial covering means virtually adapted to the oral cavity must be stretched to a significantly lesser extent than such a flat covering means, so that correspondingly gentler stretching forces are produced. Due to the only slight stretching of the covering means, it is also possible to isolate the gums together with the teeth to be treated.

The application of a rubber dam according to the invention can be carried out by one person by hand without instruments in a simple and time-saving manner, by firstly inserting the bag-shaped section of the covering means into the patient's mouth. The patient takes a short breath in through the mouth so that the covering means is pulled into a crease-free shape by the negative pressure produced. Then the annular fastening means is vertically elastically pressed together with one hand and both ends left and right are held with the other hand and are pulled backwards. The fastening means now corresponds to the spatial course of the vestibule and, with a slight swivelling, can successively be inserted laterally and carefully guided under the lower or upper lip. After release, it springs open in accordance with the shape of the individual anatomy and fixes the covering means intraorally in the above-described manner. A very good shape is produced which offers ideal conditions for treatment. The rubber dam feels pleasant to patients because the spring force makes it easier to keep the mouth open for a longer period and half the face is not covered. After insertion of the intraoral fastening means, the rubber dam stabilizes automatically and advantageously also remains stable if the patient makes dynamic oral movements, such as opening and closing, lateral movements or forward and backward movements.

In a preferred embodiment, when the rubber dam is inserted, there exists between the fastening means and the covering means an equilibrium of forces in which the fastening means is supported at least in the area of the lips by the slightly stretched covering means and is retracted or kept away from the tissue bordering the vestibule in such a way that the fastening means itself exerts no or only a slight pressure on this tissue. This means that the fastening means, as a result of its spring effect, pushes the covering means into the vestibule in the respective areas, but not so far that it is clamped under pressure between the oral mucous membrane and the fastening means. Rather, there the covering means is placed by the fastening means only lightly against the oral mucous membrane or is held "suspended" in front of this in the area of the fixing. This ensures that the transfer of force from the rubber dam to the lips, the corners of the mouth, the cheeks and the jaws is effected exclusively or at least almost exclusively via the covering means resting against the tissue and the spring effect of the fastening means is transferred indirectly via the covering means. This has the advantage that no significant direct transfer of force takes place through the annular and mostly thin fastening means to the particularly sensitive oral mucous membrane, which can make the rubber dam feel unpleasant to wear and finally lead to pressure marks. This is important in particular in the area of the lips, i.e. the front teeth, as the danger is particularly high there that a pressure is exerted in an unpleasant manner on parts of the oral mucous membrane with an osseous base or other sensitive parts. In the area of the cheeks, however, the fastening means can position or push the covering means directly against the lateral mucous membrane, an equilibrium of forces then developing between the covering means, the fastening means and the soft tissue. The fastening means is then preferably supported by the covering means in such a way that the fastening means pushes the covering means merely against the insides of the cheeks and not against the oral mucous membrane in the deepest possible course of the vestibule, but holds the covering means at a distance from the oral mucous membrane. In most cases, no great forces are required in order to push the soft tissue in the area of the cheeks laterally outwards, and the tissue is relatively insensitive with respect to such forces. In any case, it is possible to ensure that the pressure exerted by the fastening means on the oral mucous membrane is not traumatic. Instead, the transfer of force occurs over a wide area, and therefore distributed, via the covering means resting against the tissue. To this end, the covering means and the fastening means must be suitably matched with respect to each other. A large number of different factors, such as the dimensions of the two components and their mechanical properties, play a part in this matching. However, the corresponding adaptation of the fastening means and the covering means can be carried out in any case rapidly and easily by a person skilled in the art.

In a further preferred embodiment, the opening of the bag-shaped section of the covering means is round or oval. It is also advantageous if the end located opposite the opening of the bag-shaped section of the covering means is round or oval. Perpendicular to the opening, the bag-shaped section of the covering means is preferably straight-walled with parallel side walls or side walls extending conically with respect to each other. While almost any desired shapes are conceivable and possible, an efficient and inexpensive producibility is all the more guaranteed, the simpler the shape.

Furthermore, it is advantageous if the opening of the bag-shaped section of the covering means is larger than the mouth opening. As the bag-shaped section of the covering means also has a larger diameter, circular, in the tensioned state in the oral cavity than the mouth opening, the lips and the corners of the mouth are held apart in the above-described manner. The covering means can compensate for the longer path caused by the lips and the corners of the mouth only by stretching.

It is preferred that the covering means is pre-stamped, pre-marked or can be perforated as desired. The position of the teeth when the covering means is inserted is shown by the pre-punching or pre-marking. In this way or if the covering means can be perforated as desired, it is easily possible for a user to pull the covering means over one or more teeth.

Furthermore, it is advantageous if the covering means consists of latex. Such covering means have a high modulus of elasticity which provides the necessary stretchability.

In a preferred embodiment, the covering means has one or more perforations. Thus a perforation can be provided which enables breathing through the mouth if a patient has difficulty breathing through the nose. This perforation to enable breathing through the mouth is advantageously arranged in the palate area of the upper jaw. It does not interfere with the treatment because saliva and moist mucous membrane are kept away by the covering means. Furthermore, a perforation can be provided through which a saliva ejector can be inserted and fixed. However, such a perforation is normally not necessary because a patient's own saliva, which is separated by the covering means from water, blood, chemicals or other fluids or contaminations, can be swallowed as usual. If a perforation is provided for a saliva ejector, it is further advantageous to form a further perforation in the covering means in the palate area, in order that air can be subsequently sucked up through this, thus preventing a vacuum behind the covering means which would cause the covering means to press against the inside of the oral cavity.

Ring-shaped elements of different diameters can be provided as fastening means for different mouth sizes. As a result of the stretchability of the covering means, it is in a position to compensate for the size differences of the oral cavity of patients, such as for example of adults with tray sizes S, M and L, and to easily adapt to individual anatomical differences or special features, such as for example a strong musculature, macroglossia (enlarged tongue), a mouth opening that is too small or too large or a limited mouth opening. However, it is advantageous if annular fastening means which fit the respective patient are chosen. They can be colour-marked as to the spring force within the same diameter, so that all sizes and tensioning forces can be covered in a continuously variable manner. As a result of the combination of the suitably shaped covering means and different annular fastening means, a finely graduated and controllable system is created which is suited to all conditions.

The annular fastening means can be made of plastic, glass fibres or metal. It can have a round, rectangular or hexagonal cross-section. Furthermore, it can be round, elliptical, asymmetric or spatially anatomically slightly deformed, the easily producible round shape however being sufficient in most cases.

It is possible that the annular fastening means is designed to be sterilizable, disinfectable and reusable or as a disposable article.

In addition, it is also advantageous if the annular fastening means is covered by an elastic tube. This provides a protection against pressure marks. Also in order to prevent pressure marks, the annular fastening means can advantageously have small notches for the lip frenulums arranged in the middle of the upper and lower jaw. These measures are not necessary in the case of the above-described preferred embodiment, in which the fastening means is kept away by the covering means in such a way that it does not rest against the oral mucous membrane or only rests lightly against it.

In a preferred embodiment, the frame is fixedly connected to the covering means. To this end, the frame can preferably be incorporated into the covering means or glued to this. However, it is also advantageous if the frame is not fixedly connected to the covering means, but is subsequently fastened to this or is attachable, so that the state of tension of the covering means can be additionally controlled by the manner in which the frame is fastened or attached. Such a control possibility can advantageously also be realized by constructing the frame as an adjustable ring.

The frame can advantageously be made of plastic. Furthermore, it is advantageous if the frame has a slight straightening or a recess for the nose. Furthermore, it is advantageous if the frame is anatomically spherically curved to fit the shape of the face, so that the frame can lie flat against the perioral facial areas.

If one tooth or several teeth together with the gums are to be isolated, it is preferred if the rubber dam comprises an adhesive window. This has the shape of an anatomically arched frame which can be placed over the teeth and onto the alveolar process. Towards the oral cavity, this frame has retaining means, for example in the form of claws or bent-back edges, with which retaining means the covering means, which for example in comparison with the mere isolation of a tooth is perforated or punched to a somewhat larger extent, can be fastened to the adhesive window.

It is possible that the frame of the adhesive window is plastically deformable. In this case, it is advantageous if the frame comprises a material which can be cured by light irradiation. On the other hand, it is also possible for the frame to be designed elastic such that the adhesive window can be placed slightly resiliently over the teeth and onto the alveolar process. The adhesive window can be fixedly connected to the covering means. Additionally, it is advantageous if the adhesive window can be provided on its underside, i.e. towards the mucous membrane and the teeth, with a reversible adhesive suitable for moist mucous membrane and/or on the side facing the oral cavity with an adhesive which effects a tight connection between the adhesive window and the teeth or the covering means, respectively. Furthermore, it is preferred that the adhesive window on its side facing the vestibule has means which the annular fastening means can engage and thereby firmly retain the adhesive window on the teeth and the gums. With suitable technology such as for example a border wire and a matrix part which fits the profile—similar to brackets in orthodontics—forces can also be transferred laterally which press the side of the adhesive window facing the tongue and palate advantageously gently and tightly against the mucous membrane. In most cases, however, the firm vestibular retaining of the adhesive window by the annular fastening means is sufficient against the pulling forces of the covering means, because the system works only with slightly stretched covering means.

Perforated or with an adhesive window, the rubber dam according to the invention, which can be produced very simply and therefore economically, is suitable for all treatments to teeth or gums. Even extractions or implants can be carried out unhindered and in a medically correct manner in the covered state.

In the following, the invention is explained in more detail with reference to embodiments which are illustrated in the drawings.

Figure 8:
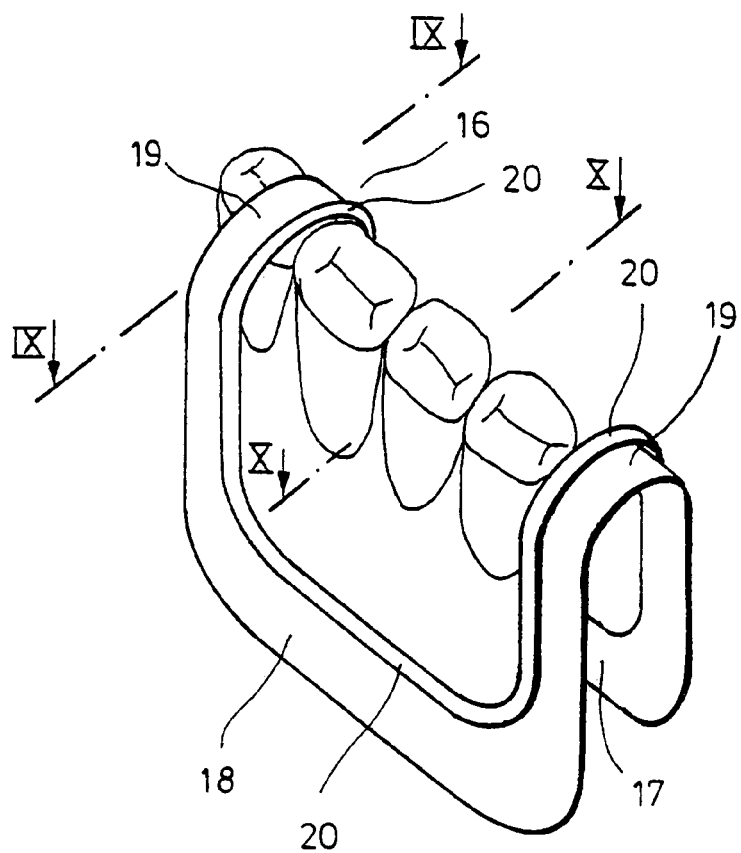
FIG. 8 shows a perspective view of an adhesive window.
Figure 8A:
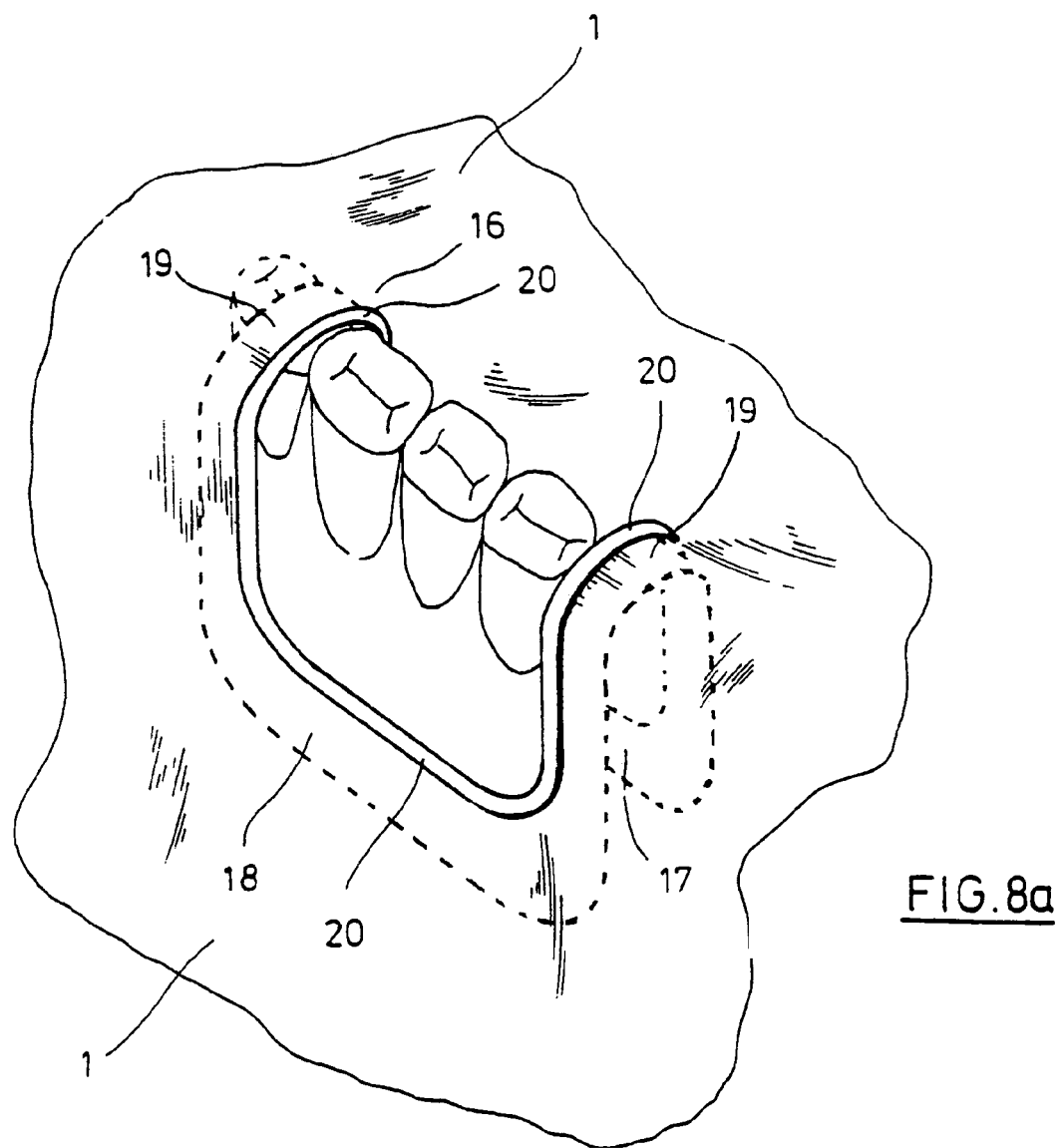

FIG. 8*a* shows a perspective view of the adhesive window from FIG. 8 after the fastening of the covering means.

Figures 9, 10:
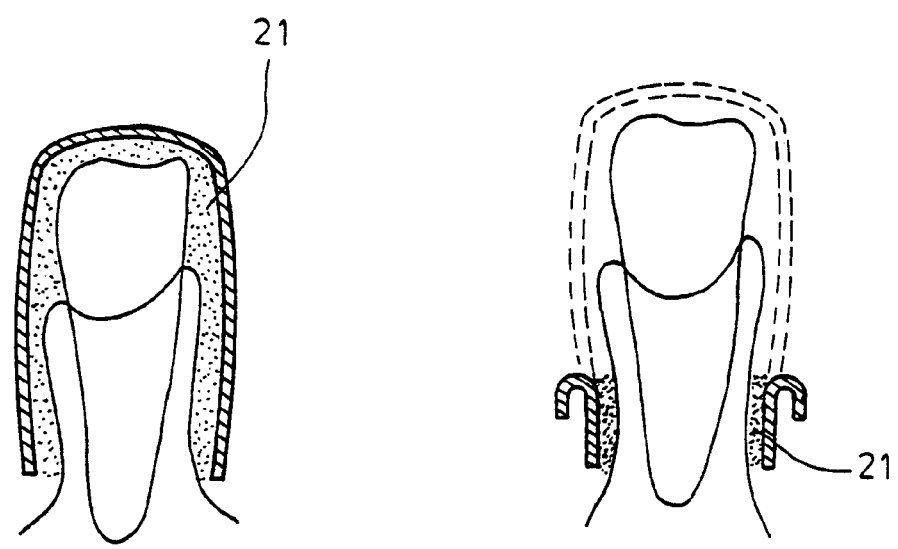

FIG. 9 shows a sectional view of the adhesive window along the line IX—IX from FIG. 8.

FIG. 10 shows a sectional view of the adhesive window along the line X—X from FIG. 8.

Figure 1:
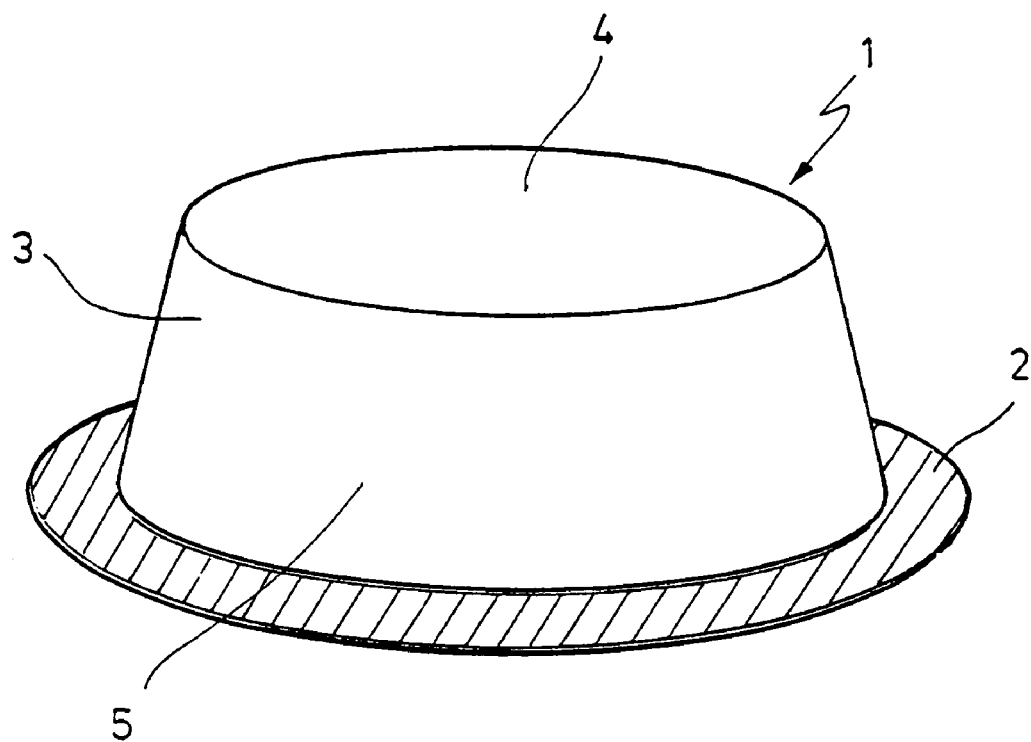
FIG. 1 shows a perspective view of a covering means connected to a frame.
Figure 2:
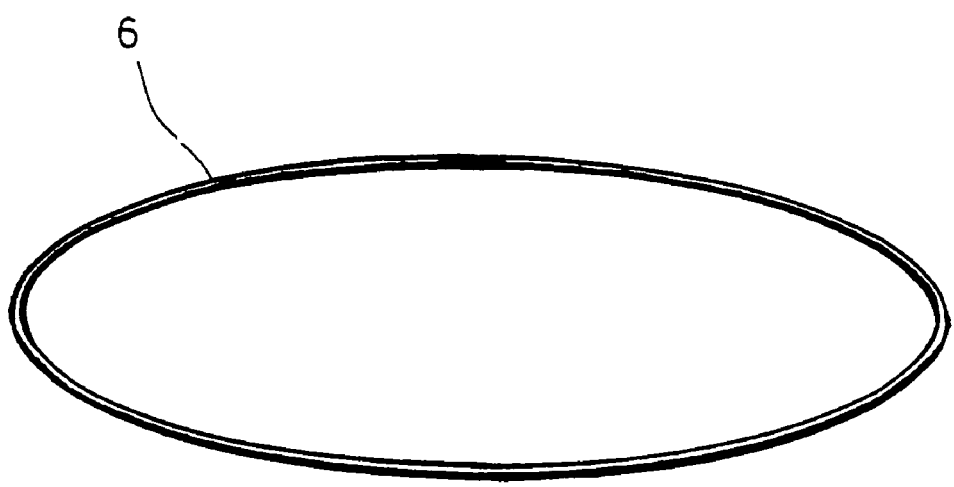
FIG. 2 shows a top view of an annular elastic fastening means.

The covering means 1 represented in perspective view in FIG. 1 is formed by a thin, flexible and elastic film-like material and is connected at its edge to a frame 2. The covering means 1 together with the frame 2 is essentially hat-shaped and has a bag-shaped section 3. The external shape of this section 3 has the design of a truncated cone, with a round opening 22, shown in FIGS. 3, 4, 5, and 7, a round base part 4 and a side wall 5 tapering towards the latter. FIG. 2 shows an annular fastening means in the shape of a circular, elastic ring 6.

In order to fasten the rubber dam in a patient's oral cavity, at first the bag-shaped section 3 of the covering means 1 is introduced into the patient's mouth and the frame 2 is placed around the mouth against the perioral facial areas. The ring 6 is then pressed together elastically such that it can be inserted into the vestibule along its entire course up to the rearmost molars. After release, the ring forces itself into the vestibule due to its elasticity, as a result of which it pushes the covering means 1 into the vestibule in the upper and lower jaw along the entire vestibule and firmly retains and fixes the covering means therein. In the process, the covering means 1 is stretched and extends in a slightly tensioned state both between the extraoral frame 2 and the vestibule and intraorally. It is apparent from FIG. 3, which shows a view of the lower jaw after the insertion of the rubber dam into the mouth, that the covering means 1 extends from the frame 2, resting against the face, along the facial skin around the corners of the mouth and the lips 7 and intraorally in the vestibule 8. The ring 6 clamped into the vestibule 8 pushes, together with the covering means 1, the upper and lower jaw vertically and the cheeks and the corner of the mouth transversally apart.

Figure 3:
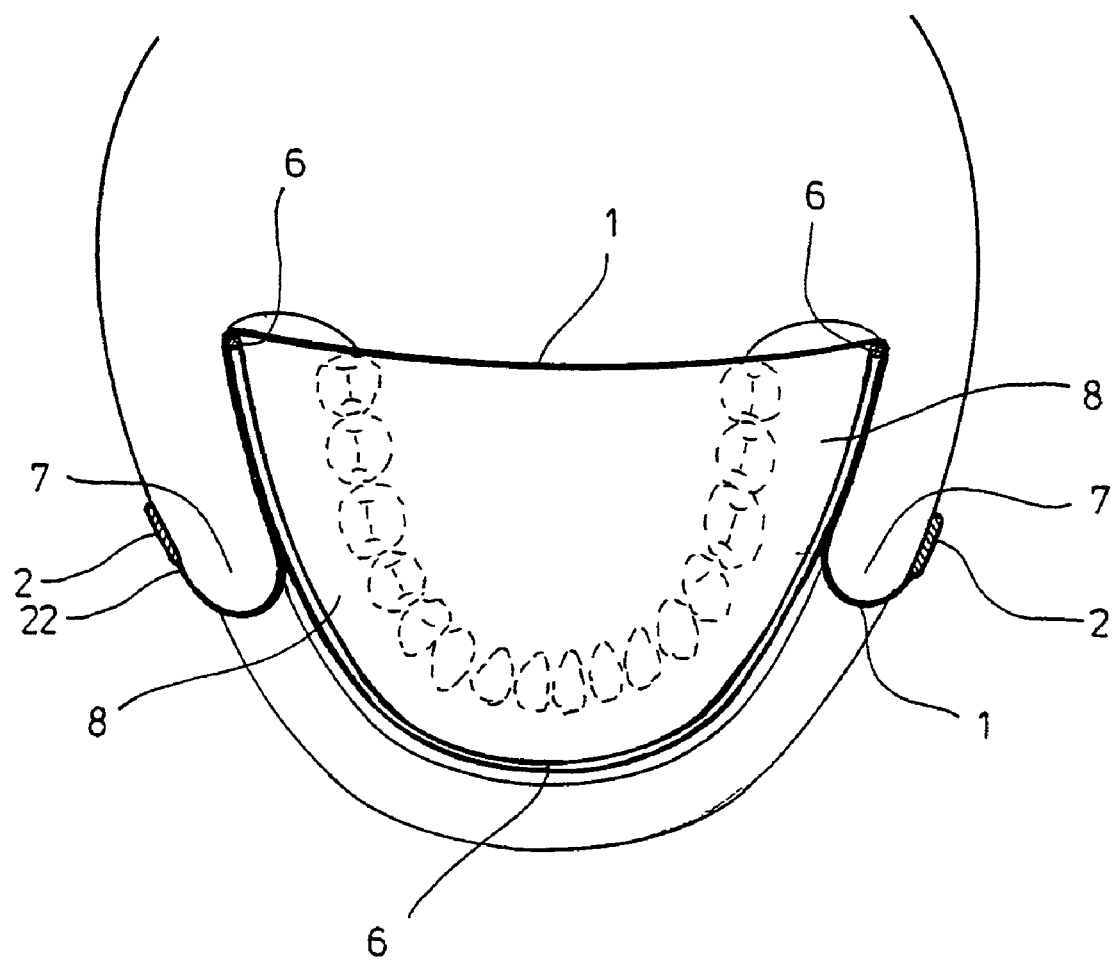
FIG. 3 shows a partly sectioned view of the lower jaw after the application of a rubber dam according to the invention.
Figure 4:
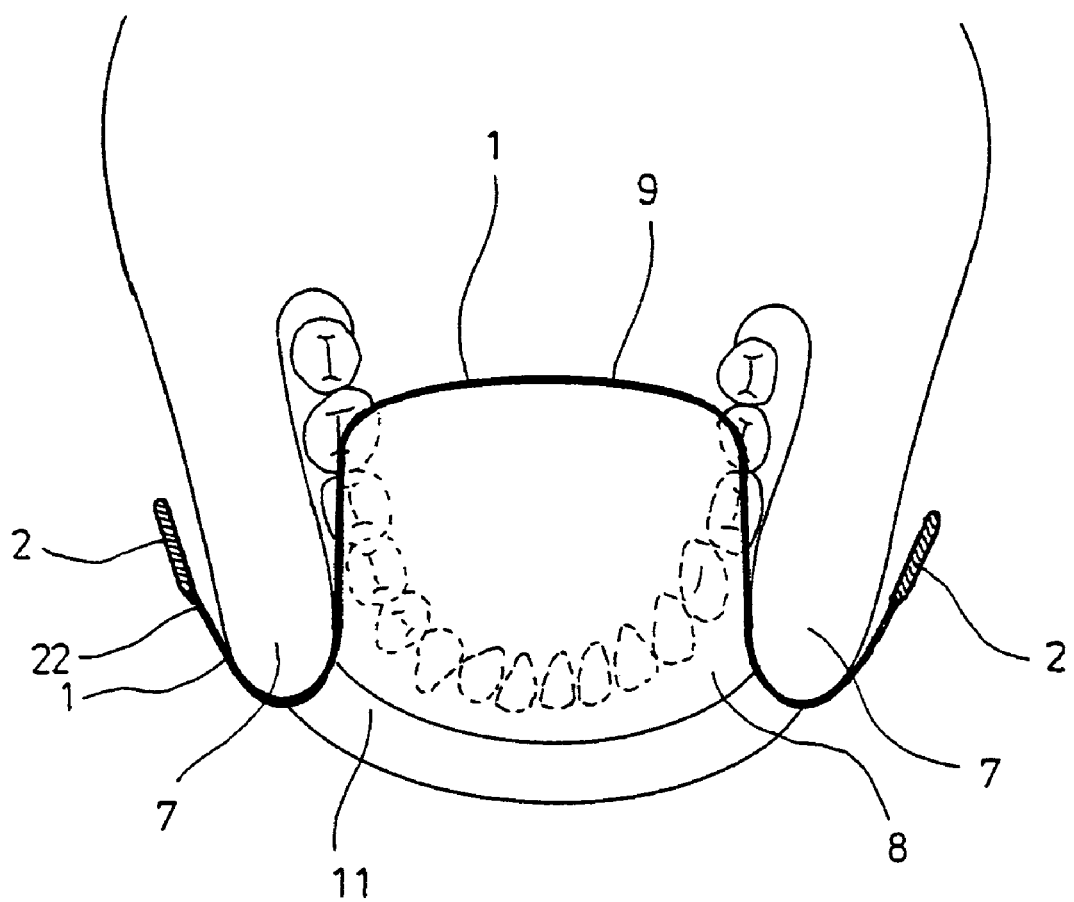
FIG. 4 shows a partly sectioned view of the lower jaw after the insertion of the covering means into the oral cavity and before the insertion of the fastening means into the vestibule.

FIG. 4 shows a view of the lower jaw after the insertion of the bag-shaped section 3 of the covering means 1 into a patient's oral cavity and before the insertion of the ring 6 into the vestibule 8. FIG. 4 therefore shows in comparison with FIG. 3 the shape 9 of the covering means 1 arranged in the oral cavity in an untensioned state before it is brought into the slightly stretched shape (FIG. 3) with the help of the ring 6 and expands the vestibule 8. The covering means 1 is constructed such that the opening 22 of the bag-shaped section 3 is larger than the mouth opening 11. At the same time, the dimensions of the bag-shaped section 3 are chosen such that it is smaller in an untensioned state than the area of the oral cavity to be isolated. In the present case, the depth of the section 3 in an untensioned state is less than the distance between the lips and the rearmost point of the vestibule in the area of the molars, and the diameter of the section 3 is smaller than the distance between the vestibule sections in the area of the side teeth of the lower jaw and the upper jaw. In any case, it is important that the dimensions of the untensioned shape 9 are chosen such that, after the insertion of the ring 6 into the vestibule, the covering means 1 is only slightly stretched regardless of the exact mouth size, i.e. with a small mouth a sufficient wall tension remains in order to prevent a sucking in by a suction device and with a large mouth, even with the greater stretching which is then necessary, no traumatic forces occur. Taking these factors into account, the covering means can be made in standard sizes, for example for children and for adults.

Figure 5:
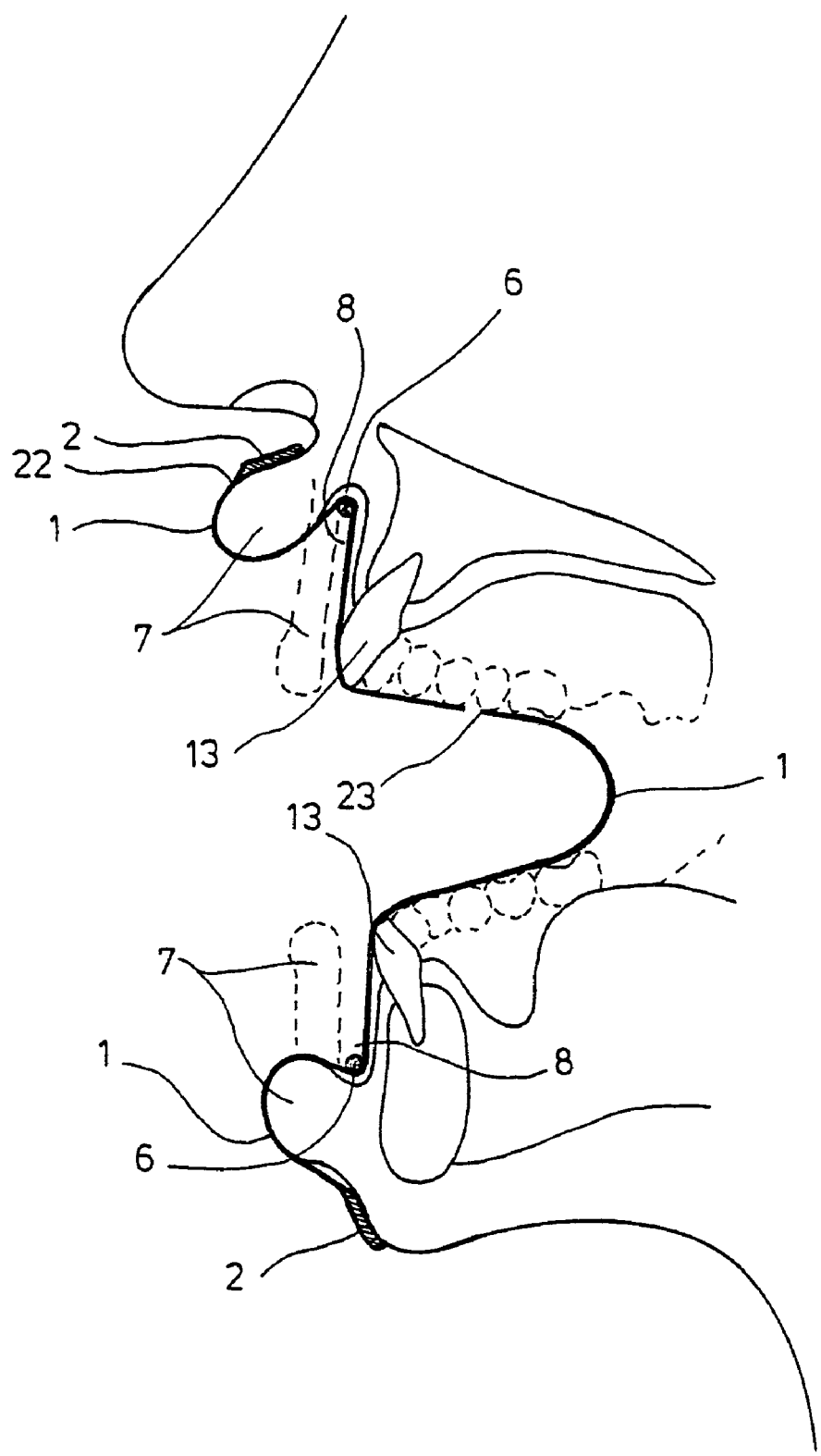
FIG. 5 shows a median section through the oral cavity after the application of a rubber dam according to the invention.

The comparison between FIGS. 3 and 4 illustrates the difference between the space taken up by the untensioned covering means 9 and the larger isolation area achieved after the insertion of the ring 6. The covering means 1 must compensate for this difference by stretching, as a result of which it is brought into a slightly tensioned shape. As the covering means 1 as described is not constructed to have the anatomically correct form and with sufficient material reserves for the smaller mouth opening, it is apparent that the covering means 1 extends around the corners of the mouth and the lips 7 in a tensioned state, because the covering means 1 can compensate for the longer path caused by the corners of the mouth and the lips 7 only by stretching. As illustrated in FIG. 5, the covering means 1 guided in a tensioned state around the corners of the mouth and the lips 7 causes the lips 7 and the corners of the mouth to be held apart spherically. In addition to the barrier function, the covering means 1 can therefore also fulfil the important task of circular retraction of the perioral tissue.

Figure 6:
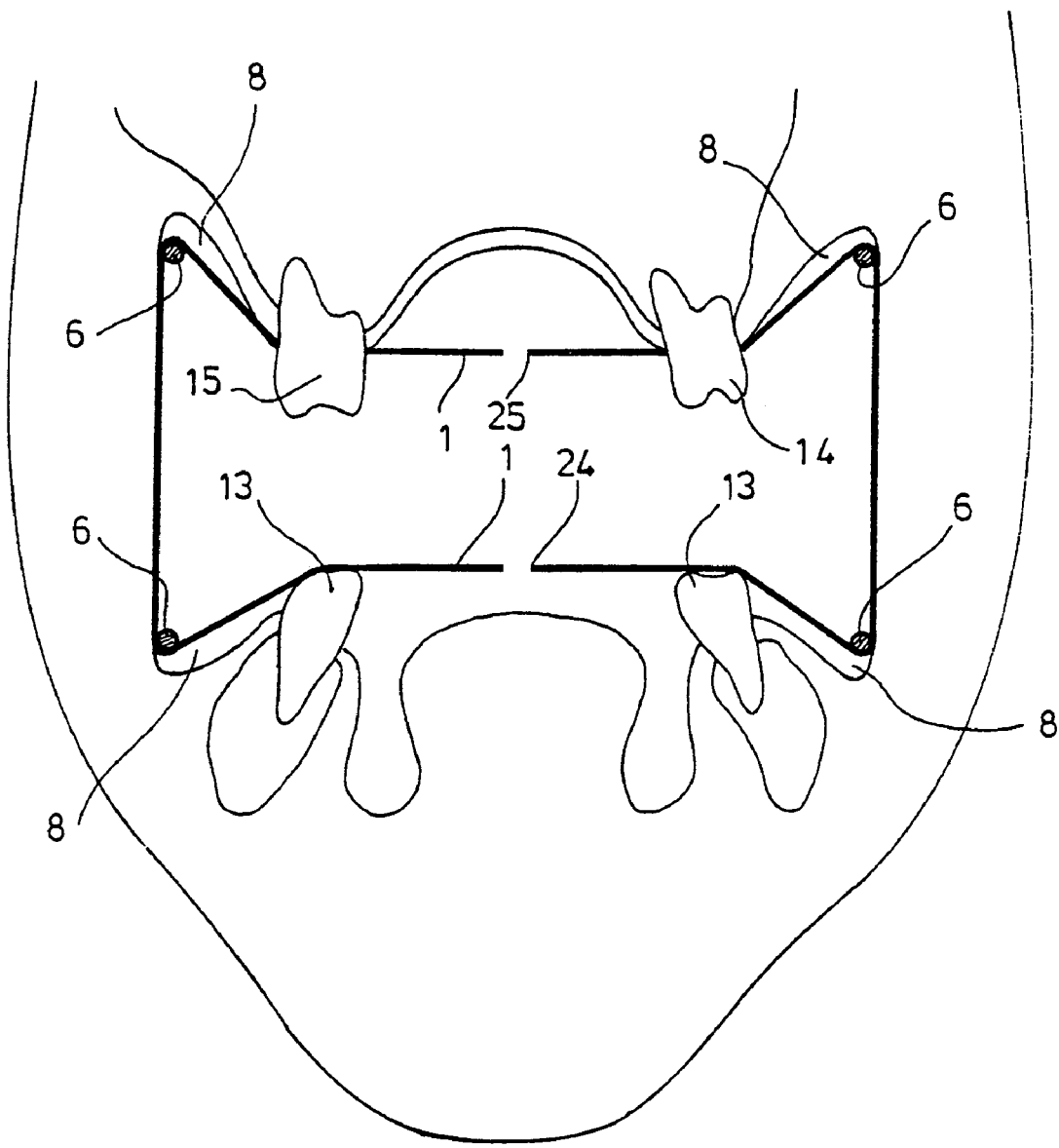
FIG. 6 shows a cross-section of the oral cavity after the application of a rubber dam according to the invention, the rubber dam being perforated on the left and right in the upper jaw and pulled over a tooth.

In addition to FIG. 5, FIG. 6 in particular shows that the covering means 1 extends intraorally out of the vestibule 8, over the front sides of the teeth 13 and their chewing surfaces. In the palate and tongue area, the covering means 1 extends in a slightly tensioned state in the plane of the chewing surfaces of the teeth 13, so that the tongue and the palate are not touched. The covering means leaves this plane only in the area of teeth 14, 15 to be isolated.

Figure 7:
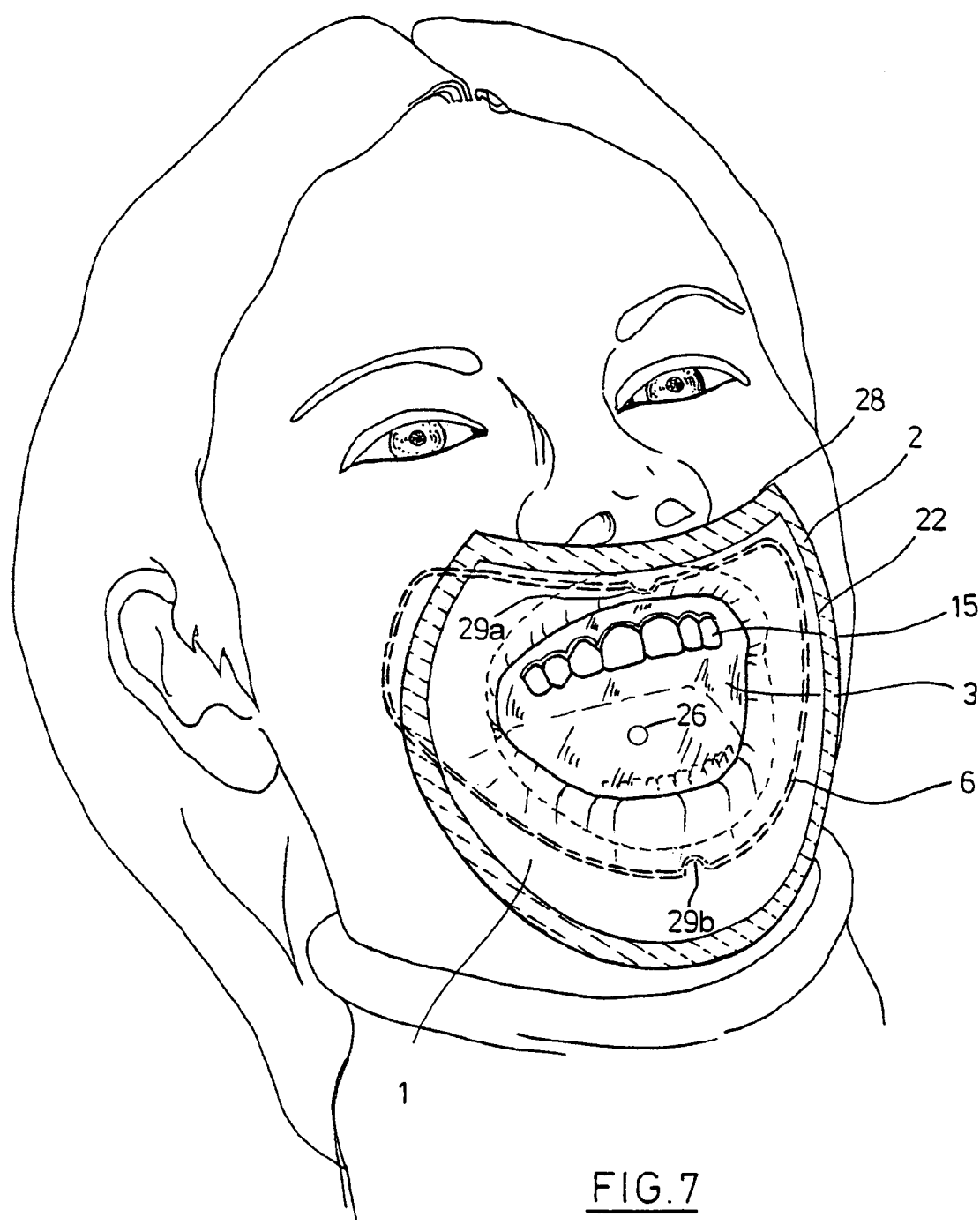
FIG. 7 shows a view of a patient's head after the application of a rubber dam according to the invention.

In FIG. 5, the covering means 1 is shown with a perforation 23 in order to enable breathing through the mouth. The perforation 23 is located in the palate area of the upper jaw. By contrast, FIG. 7 shows a covering means 1 having a perforation 26 for enabling breathing through the mouth located in the area of the lower jaw. In FIG. 6, the covering means 1 is shown with a perforation 24 for a saliva ejector, and a perforation 25 for the subsequent suction of air.

Furthermore, it is represented in FIGS. 5 and 6 that the ring 6 pushes the covering means 1 only so far into the vestibule 8 that the covering means 1 is not firmly clamped at the deepest point of the vestibule 8 between the ring 6 and the oral mucous membrane. Rather, the ring 6 "is suspended" in the area of the lips in the vestibule 8 and is supported by the covering means 1 such that the ring exerts no direct pressure on the tissue (see FIG. 5), and extends in the area of the cheeks spaced from the oral mucous membrane in the deepest possible course (see FIG. 6). This is achieved by the fact that the spring effect of the ring 6 and the stretchability of the covering means 1 are suitably adapted to each other. As is apparent from FIG. 6, only in the area of the cheeks the ring 6 pushes the covering means 1 directly laterally against the oral mucous membrane and therefore together with the covering means 1 the cheeks apart. In this area, in which an equilibrium of forces is established between the ring 6, the covering means 1 and the soft tissue, the pressure is however not as critical, as soft tissue is involved which can be easily pushed outwards and as a result of the lack of an osseous base is relatively insensitive. Depending on the structure of the cheeks, the vertical course of the covering means 1, represented in FIG. 6, between the fixings in the upper jaw and in the lower jaw effected by the ring 6 may also be not straight, but curved inwards slightly towards the teeth as a result of the counterpressure of the soft tissue.

In FIG. 7, the patient's head is shown after the application of the rubber dam. As a result of the stretching of the covering means 1 and the fixing elements 2 and 6, the rubber dam stabilizes itself automatically after the insertion of the intraoral fastening means 6. If it is established during application that the ring 6 is too large or too small, it can be quickly replaced by another one. It is essential that this thin ring 6 lies almost invisible in a zone which does not disturb the person performing the treatment, and nevertheless makes the passive shape 9 of the covering means 1 into a slightly tensioned covering of the isolation area and makes the oral cavity into a pleasant operating area.

As shown in FIG. 7, a slight straightening or recess 28 for the nose is provided in the frame 2. Further, the annular fastening means 6 has small notches 29a and 29b for the lip frenulums arranged in the upper and lower jaw.

In FIG. 8, an adhesive window 16 is represented which is used if a tooth or several teeth together with the gums are to be isolated. The adhesive window 16 has two lateral sections 17, 18 which extend parallel to each other and which are connected at their ends by two arcuate sections 19. The dimensions are chosen such that the adhesive window 16 as an anatomically shaped frame can be placed with the arches 19 over the teeth and the lateral sections 17, 18 onto the alveolar process in such a way that one or more teeth as well as a part of the adjoining gum is freely accessible between the arches 19 of the window 16.

It is apparent from FIG. 9, which shows a section through the adhesive window 16 placed onto the teeth along the line IX–IX from FIG. 8, that the adhesive window 16 is provided at its side facing the teeth with an adhesive 21, so that a safe and tight connection between the adhesive window 16 and the teeth and the gum is guaranteed.

At the edge, lying within the area delimited by the adhesive window 16, of the frame sections 17, 18, 19, claws 20 are provided which are formed by bent-back areas of the frame sections 17, 18, 19 and on which the covering means 1 can be fastened. This is illustrated in FIG. 10 which shows a section through the adhesive window 16 placed onto the teeth along the line X—X from FIG. 8. These claws 20 can be provided along all the inside edges of the frame sections 17, 18, 19. In order to fasten the covering means 1 to the adhesive window 16, the covering means 1 is perforated and placed over the adhesive window such that the edges of the perforation are grasped by the claws 20 and the perforation is kept in an expanded state (see FIG. 8a). However, it is also possible that the claws 20 are provided merely on the inside edges of the horizontal frame sections 17, 18 and the sealing along the arch sections 19 takes place by the fact that the covering means rests against these in a tensioned state. In this case, the arch sections 19 can also be provided on their surface with an adhesive which assists this sealing.

What is claimed:

1. Rubber dam for the isolation of a tooth or several teeth in a patient's mouth comprising an frame for resting against the perioral facial area, an elastic film-like covering means which can be connected to the frame and in an untensioned state has a bag-shaped section for insertion into the oral cavity, and a fastening means for the intraoral fastening of the covering means,
    wherein
    the fastening means is formed by an elastic and annular element which is adapted in order to be inserted in an elastically deformed state into the vestibule and to exert a force on the covering means which pushes the covering means into the vestibule and firmly retains it therein, so that, when the rubber dam is inserted, the covering means extends in a slightly tensioned state between the frame and the fastening means located in the vestibule around the lips and the corners of the mouth and intraorally in the upper jaw and in the lower jaw in a slightly tensioned state out of the vestibule, over the external surfaces and chewing surfaces of the teeth and in the palate and tongue area in the plane of the chewing surfaces, and the lips, cheeks and corners of the mouth are pushed away from the teeth and a force directed upward is exerted on the upper jaw and a force directed downward is exerted on the lower jaw.

2. Rubber dam according to claim 1, wherein, when the rubber dam is inserted, an equilibrium of forces develops between the covering means and the fastening means, in which equilibrium the fastening means is supported by the slightly tensioned covering means such that, at least in the area of the lips, the fastening means does not press or only lightly presses against the tissue bordering the vestibule and the transfer of force from the rubber dam to the lips, the corners of the mouth, the cheeks and the jaws takes place via the covering means.

3. Rubber dam according to claim 1 wherein the opening of the bag-shaped section of the covering means is round or oval.

4. Rubber dam according to claim 1, wherein the end located opposite the opening of the bag-shaped section of the covering means is round or oval.

5. Rubber dam according to claim 1, wherein the bag-shaped section of the covering means is straight-walled or conical.

6. Rubber dam according to claim 1, wherein the opening of the bag-shaped section of the covering means is larger than the mouth opening.

7. Rubber dam according to claim 1, wherein the covering means is pre-stamped, pre-marked or can be perforated as desired.

8. Rubber dam according to claim 1, wherein the covering means consists of latex.

9. Rubber dam according to claim 1, wherein the covering means has a perforation in order to enable breathing through the mouth.

10. Rubber dam according to claim 9, wherein the perforation for breathing through the mouth is located in the palate area of the upper jaw.

11. Rubber dam according to claim 9, wherein the perforation for breathing through the mouth is located in the area of the lower jaw.

12. Rubber dam according to claim 1, wherein the covering means has a perforation for a saliva ejector.

13. Rubber dam according to claim 12, wherein the covering means has a perforation for subsequent suction of air.

14. Rubber dam according to claim 1, wherein annular elements of different diameter are provided as fastening means for different mouth sizes.

15. Rubber dam according to claim 1, wherein the annular fastening means has a round, rectangular or hexagonal cross-section.

16. Rubber dam according to claim 1, wherein the annular fastening means is round, elliptical, asymmetric or spatially anatomically slightly curved.

17. Rubber dam according to claim 1, wherein the annular fastening means is made of plastic, glass fibers or metal.

18. Rubber dam according to claim 1, wherein the annular fastening means is sterilizable or disinfectable and reusable.

19. Rubber dam according to claim 1, wherein the annular fastening means is produced as a disposable article.

20. Rubber dam according to claim 1, wherein the annular fastening means is covered by an elastic tube.

21. Rubber dam according to claim 1, wherein the annular fastening means has small notches for the lip frenulums.

22. Rubber dam according to claim 1, wherein the frame is fixedly connected to the covering means.

23. Rubber dam according to claim 22, wherein the frame is incorporated into the covering means or adhesively connected to the covering means.

24. Rubber dam according to claim 1, wherein the frame is made of plastic.

25. Rubber dam according to claim 1, wherein the frame has a slight straightening or a recess for the nose.

26. Rubber dam according to claim 1, wherein the frame is an adjustable ring.

27. Rubber dam according to claim 1, wherein the frame is anatomically spherically curved to fit the shape of the face, so that the frame can flatly abut.

28. Rubber dam according to claim 27, wherein the retaining means are claws or bent-back edges.

29. Rubber dam according to claim 1, further comprising an adhesive window for the joint isolation of teeth and gums in the form of an anatomically curved frame which can be placed over the teeth and onto the alveolar process and, on the side facing away from the teeth, has retaining means with which the covering means can be fastened to the adhesive window.

30. Rubber dam according to claim 29, wherein the frame is plastically deformable.

31. Rubber dam according to claim 30, wherein the frame comprises a material which can be cured by light radiation.

32. Rubber dam according to claim 29, wherein the frame is designed to be elastic such that the adhesive window can be placed slightly resiliently over the teeth and onto the alveolar process.

33. Rubber dam according to claim 29, wherein the adhesive window can be provided towards the mucous membrane and the teeth with a reversible adhesive suitable for moist mucous 34. Rubber dam according to claim 29, wherein the adhesive window is fixedly connected to the covering means.

35. Rubber dam according to claim 29, wherein the adhesive window, facing the vestibule, comprises means through which the annular fastening means can firmly retain the adhesive window on the teeth.

36. Rubber dam according to claim 29, wherein the adhesive window can be provided on the side facing the oral cavity with an adhesive which effects a tight connection with the covering means.

* * * * *